US006287573B1

(12) United States Patent
Mendoza

(10) Patent No.: US 6,287,573 B1
(45) Date of Patent: *Sep. 11, 2001

(54) **METHOD AND VACCINE FOR TREATMENT OF *PYTHIOSIS INSIDIOSI* IN HUMANS AND LOWER ANIMALS**

(75) Inventor: Alberto L. Mendoza, Haslett, MI (US)

(73) Assignee: Board of Trustees operating Michigan State University, East Lansing, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/082,232

(22) Filed: May 20, 1998

Related U.S. Application Data

(62) Division of application No. 08/895,940, filed on Jul. 17, 1997, now Pat. No. 5,948,413.

(51) Int. Cl.$^7$ .......................... A61K 39/02; A61K 39/38; A61K 38/00; C07K 14/00; C07K 17/00
(52) U.S. Cl. ................................. 424/234.1; 424/184.1; 424/235.1; 514/20; 530/350; 530/300
(58) Field of Search .............................. 424/184.1, 234.1, 424/235.1; 514/20; 530/350, 300

(56) References Cited

U.S. PATENT DOCUMENTS 5,948,413 * 9/1999 Mendoza .

OTHER PUBLICATIONS

Mendoza et al. J. Clin. Microbial, 30/11:2980–2983, 1992.*
Mendoza et al. Mycopathologia, 119:89–95, 1992.*
Newton et al. The Compendium, 15:491–493, 1993.*
Miller et al. JAVMA, 182/11:1227–1229, 1983.*
Mendoza et al, J. Clin. Microbiol. 23/5:813–816, 1986.*
Patton et al J. Vet. Internal Med. 10/3: 139–142, 1996.*
Mendoza et al, Mycopathologia 104:59–62, 1988.*
Fraco et al, Australian + New Zealand J. Ophthalmol, 25:177–179, 1997.*
Mendoza et al, J. Medical + Vet. Mycology 26:5–12, 1988.*
Thitithanyanont et al, Clin. Inf. Diseases 27:1394–1400, 1998.*
Mendoza et al, Clin. + Diagn.Lab. Immunol 4/6: 715–718, 1997.*
Santurio, et al, Mycopathologia 141: 123–125, 1998.*
Imwidthaya Postgrad. Med. J. 70:558–560, 1994.*
Mendoza et al J. Mycol. Med. 6:151–164, 1996.*
DeCock,W.A.M, et al., J. Clin. Microbiol. 25:344–349 (1987).
Mendoza, L., et al., Equine pythiosis in Costa Rica: report of 39 cases, Mycopathologia 94:123–129 (1986).
Miller, R. I., Aust. Vet. J. 57:377–382 (1981).
Newton, J. C., et al., The Compendium 15:491–493 (1993).
Gudding R., et al., Can. Vet, J. 36:302–306 (1995).
Pier, A. C., Equine Practice 15:23–27 (1993).
Miller, R. I., et al., J. Am. Vet. Med. Assoc. 182:1227–1229 (1983).
Mendoa, L., et al., Mycopathologia 119:89–95 (1992).
Mendoza, L., et al., J. Clin. Microbiol. 30:2980–2983 (1992).
Cohen, J., Science 264:503–505 (1994).
Chetchotisakd, P., et al., J. Med Assoc Thailand 75:248–254 (1992).
Wanachiwanawin, W., et al., Trans Royal Soc Trop Med Hyg 87:296–298 (1993).
Burke, D., S., Vaccine 11:883–890 (1993).
Convit. J., et al., Trans Royal Soc Trop Med Hyg 87:444–448 (1993).
Stanford, J.L., Trop Geograp Med 46:93–107 (1994).
Rinaldi, M.G., et al., Phythium insidiosum causes severe disease in a healthy boy. Mycology Observer 9:7 (1989).
Thianprasit, M., Human pythiosis. Trop Dermathol 4:1–4 (1990).

* cited by examiner

*Primary Examiner*—Nita Minnifield
(74) *Attorney, Agent, or Firm*—Ian C. McLeod

(57) ABSTRACT

A method and vaccine for treatment of pythiosis in humans and animals is described. In particular a vaccine comprising a mixture of extracellular and intracellular proteins is described. The vaccine enables cures of chronic pythiosis in some patients.

8 Claims, No Drawings

METHOD AND VACCINE FOR TREATMENT OF *PYTHIOSIS INSIDIOSI* IN HUMANS AND LOWER ANIMALS

CROSS-REFERENCE TO RELATED APPLICATION

This application is a divisional of application Ser. No. 08/895,940, filed Jul. 17, 1997, now U.S. Pat. No. 5,948,413.

BACKGROUND OF THE INVENTION (1) Summary of the Invention

The present invention relates to protein vaccines and methods of use thereof for the treatment of *Pythium insidiosum* infections in humans and lower mammals. Further, the present invention relates to a method for preparing the preferred vaccine for the treatment which contains intracellular and extracellular proteins of *Pythium insidiosum*.

(2) Description of Related Art

Infections caused by fungal and parafungal organisms are occurring with increasing frequency in patients with debilitating illnesses such as leukemia and AIDS, as well as those undergoing immunosuppressive therapy. Within this group of organisms are the traditional pathogenic fungi and a long list of newly recognized emerging opportunistic fungal and parafungal organisms. Among the emerging pathogens is the oomycete *Pythium insidiosum* a fungal-like organism in the Kingdom Kromista, Phylum Pseudofungi. *Pythium insidiosum* is not only psychologically distinct from members of the Kingdom Fungi, but also differs physiologically. This may explain why anti-fungal drugs do not have any effect on pythiosis.

Pythiosis insidiosi particularly occurs in humans and lower animals in the tropical, subtropical, and temperate areas of the world (Cock, W. A. W., et al., J. Clin. Microbiol. 25:344–349 (1987)). The disease was described in the beginning of the century in equines of tropical and subtropical countries including India and Indonesia as well as the USA. Soon, however, it was evident that the disease not only affected equines but other mammalian species. In lower animals infections of the cutaneous tissues, lymphatic vessels, intestines, lungs, and bones have been found. In humans, a deadly arteritis infection, subcutaneous invasion and keratitis occurs.

The currently available drugs used to treat fungal infections have had little or no effect on *Pythium insidiosum*. Reports of treatment with either amphotericin B or surgery, commonly used to treat this disease in both humans and lower animals, have indicated that 60% of the patients died of their infections. In cases of arterial invasion in humans, amphotericin B did not eliminate the infection (Rinaldi, M. G., et al., Mycology Observer 9:7 (1989); and Thianprasit, M., Trop Dermathol 4:1–4 (1990)), whereas in surgery the main problem has been to determine how much of the infected tissues has to be removed. Thus, relapses are common in surgically treated patients, who must also endure the pain and distress that such an invasive traumatic procedure inflicts on them.

The curative properties of *P. insidiosum* possessed curative properties was first noticed when Costarrican equine with pythiosis injected with *P. insidiosum* antigens, in a skin test, resulted in the cure of some of the horses (Mendoza, L., et al., Equine pythiosis in Costa Rica: report of 39 cases. Mycopathologia 94:123–126 (1986)). Simultaneously, a similar vaccine with curative properties was successfully used in equines with the disease in Australia (Miller, R. I., Aust. Vet. J. 57:377–382 (1981)). These two vaccines have been referred to in the literature as Mendoza's and Miller's vaccines respectively (Newton, J. C., et al., The Compendium 15:491–493 (1993)). Early reports indicated that the antigens used in the *P. insidiosum*-vaccine possessed unique characteristics, somewhat similar to the features of those reported in Trichophyton verrucosum (Gudding R., et al., Can. Vet. J. 36:302–306 (1994)) and other immunotherapeutic vaccines (Foster, J. S., et al., Vet. Med. Small Ani. Clin. 71, 920 (1976); Pier, A. C., et al., Equine Practice 15:23–27 (1993)).

Miller's vaccine uses sonicated hyphal antigens (Miller, R. E., Aust. Vet. J. 57:377–382 (1981)), while Mendoza's vaccine is prepared from culture filtrate antigens (Mendoza, L., et al., 94:123–126 (1986)). Both vaccines have cured about 53% of vaccinated horses. Mendoza's vaccine, however, has a longer shelf life and milder side effects (Miller, R. I., et al., J. Am. Vet. Med. Assoc. 182:1227–1229 (1983)). In addition to its immunotherapeutic features Mendoza's vaccine also showed some degree of protection. This protection was later found to be of short duration (Mendoza, L., et al., Mycopathologia 119:89–95 (1992)). In 15 years of use more than 300 equines have been cured. Mendoza's vaccine was proved to be consistent and safe. In spite of this, the vaccine only cured early equine pythiosis, but not chronic cases of this disease (Mendoza, L., et al., Mycopathologia 119:89–95 (1992)). Aside from the fact that the vaccine only cured early equine pythiosis cases, nothing was known about the immunogens involved in its curative properties nor the immune mechanisms that triggered the killing of *P. insidiosum*'s hyphae infected tissues.

In a recent study using SDS-PAGE and Western blot analysis, the presence of three immunodominant hyphal proteins was found to be of interest (Mendoza, L., et al., J. Clin. Microbiol. 30:2980–2983 (1992)). The immunoblotting study revealed that the IgG of sera from horses with active pythiosis recognized most of the proteins of *P. insidiosum*. However, of all the proteins analyzed, three bands, the 32,000-molecular-weight 32K, 30K, and 28K, were particularly prominent. More significantly was the finding that antibodies against these three proteins persisted for long periods of time in the successfully vaccinated horses.

There is a need for vaccines which cure pythiosis. The need is particularly great where the patient is in the chronic stage of the disease.

OBJECTS

It is therefore an object of the present invention to provide a method for treating pythiosis in humans and lower animals. Further, it is an object of the present invention to provide vaccine compositions and methods for the preparation thereof. Further still, it is an object of the present invention to provide a method for curing pythiosis which is economical, reliable and effective. These and other objects will become increasingly apparent by reference to the following description.

DESCRIPTION OF PREFERRED EMBODIMENTS

The present invention relates to an injectable vaccine for treatment of pythiosis which comprises in a sterile aqueous solution an admixture of: (a) intracellular proteins separated from disrupted cells of *Pythium insidiosum*; and (b) extracellular proteins from a supernatant from growing the cells of the *Pythium insidiosum*.

Further, the present invention relates to a method for providing an injectable vaccine for treatment of Pythiosis which comprises: (a) growing cells of *Pythium insidiosum* in a culture medium; (b) separating the cells from a first supernatant of the culture medium which contains extracellular proteins; (c) killing the cells; (d) disrupting the cells in sterile water; (e) separating the disrupted cells from the water to produce a second supernatant containing intracellular proteins; (f) mixing the first supernatant of step (b) with the second supernatant of step (e); (g) separating the combined proteins from the mixture of step (f); (h) mixing the separated proteins in sterile distilled water; and (i) dialyzing the mixture of step (h) to remove low molecular weight components less than 10,000 MW to produce the vaccine.

Further, the present invention relates to a method for the treatment of Pythiosis in a mammal having the disease which comprises: (a) providing an injectable vaccine which comprises in a sterile aqueous solution in admixture: (1) an intracellular proteins separated from disrupted cells of *Pythium insidiosum*; and (2) extracellular proteins from a supernatant from growing the cells of the *Pythium insidiosum*; and (b) vaccinating the mammal with the vaccine.

Finally, the present invention relates to a method for treatment of pythiosis in human patients having the disease which comprises: (a) providing a vaccine containing separated proteins of *Pythium insidiosum* in a sterile aqueous solution; and (b) vaccinating the patient with the vaccine.

The *Pythium insidiosum* was deposited with the American Type Culture Collection under the Budapest Treaty as ATCC 74446. It is available upon request by name and number. All restrictions on distribution of ATCC 58643 are irrevocably removed on granting of a patent on this application. The address of the American Type Culture Collection is 10801 University Blvd., Manassas, Va. 20110–2209.

Preferably the vaccine contains between about 3.0 and 2.0 mg of protein per ml. The vaccination dosage is between about 1.0 and 2.0 mg per kg of body weight of the mammal.

The vaccine of the present invention is preferably injected intramuscularly. The vaccine can also be administered intradermally or subcutaneously.

A sterile carrier or adjuvant is used in the vaccine. The preferred carrier is water or an aqueous saline solution, particularly in humans. An adjuvant for the vaccine is EMULSIGEN (MVP Labs, Ralston, Nebr.), which is a paraffin oil in a water emulsion, which can be used in food animals. Freund's Incomplete Adjuvant, which is 15 percent by weight mannide monooleate and 85% paraffin oil, available from Difco, Detroit, Mich., can be used in non-food (i.e. laboratory animals). The adjuvants aid in slowly releasing the vaccine into the animal and can potentiate the immune response. Any commercial oil emulsion adjuvants can be used such as vitamin E.

The vaccine can be combined with nonimmunizing components for other diseases to produce a multivalent vaccine or with other medicaments, particularly antibiotics. The antibiotics can be used prior to vaccination.

In the following Example 1, the improved vaccine was prepared by adding cytoplasmic antigens to the earlier *P. insidiosum*-vaccine (Mendoza et al., Mycopathologica 119:89–95 (1992)). In Example 2, the modified vaccine of Example 1 was tested in horses with chronic pythiosis insidiosi, only 48% of the horses were cured. All horses with acute pythiosis insidiosi were cured with this new vaccine. One advantage of the new vaccine is that the earlier vaccine always failed in chronic cases. Example 3 shows preparation of the proteins by recombinant methods. In Example 4, the modified vaccine was successfully tested in a Thai boy with pythiosis insidiosi. This Thai patient was diagnosed with an infection caused by *P. insidiosum* in his external carotid artery. In spite of efforts to treat the infection with traditional methods the patient did not show improvement. As a last resort *Pythium insidiosum* modified vaccine was given to him. The patient has been declared clinically cured.

EXAMPLE 1

1. *Pythium insidiosum* strain ATCC 74446, was transferred to a 1.0-liter flask containing 500 ml of Sabouraud dextrose broth (Difco, Detroit, Mich.).

2. Cultures were incubated at 37° C. for five days on shaker rotating at 150 rpm.

3. Cultures were killed with Merthiolet (thimersol) (0.02% wt/vol), filtered to separate the cells (hyphae) from the liquid phase containing exoantigens of *P. insidiosum* (save the liquid phase in a sterile container to be used in step 6).

4. The cell mass obtained in step 3, was washed twice with sterile distilled water disrupted by sonication until 100% of the hyphae were fragmented. Other methods could be used such as a French press.

5. The mixture, obtained in step 4, was centrifuged at 5,000×g for 20 minutes.

6. The supernatant was separated from the pellet (pellet can be eliminated) and then the supernatant was added to the liquid phase in step 3.

7. To confirm the presence of the immunodominant proteins in the supernatant obtained on step 6, the sample was subjected to SDS-PAGE electrophoresis and Western blot analysis as per Mendoza et al (J. Clin. Microbiol. 30:2980–2983 (1992)). Following electrophoresis, the prominent proteins were cut from the acrylamide gels and purified. A mixture of the three proteins were added to Mendoza's original vaccine (~2.0 µg/ml final concentration). A western blot analysis was then performed on the vaccine to verify the presence of the three proteins.

8. After visualization of the immunodominant proteins, the mixture was then precipitated with an equal volume of acetone and pelleted at 20,000×g for 30 minutes in a refrigerated centrifuge.

9. The pellet was resuspended in sterile distilled water at ~2.0 mg/ml protein concentration.

10. The mixture was dialyzed using a membrane cut off point of 10,000 MW.

11. The sterility of the vaccine was confirmed by culturing 100 µl of the mixture on blood agar and Sabouraud dextrose broth.

12. The vaccine was stored at 4° C. until use.

EXAMPLE 2

One major drawback in evaluating the *P. insidiosum*-vaccine is the lack of an animal model. The only animal in which the disease can be successfully reproduced is the rabbit (*Orcytologous cuniculus*). But, no systematic studies have been conducted to evaluate its effectiveness as an experimental model. Evaluations of the *P. insidiosum*-vaccine has been carried out only in horses with the disease. The diagnosis of pythiosis in the treated equines was verified either by serology and/or culture, and by histopathology or all. Based on the fact that neither Miller's nor Mendoza's original vaccines cured infected horses after 60 days or more of infection, seven horses were selected with chronic pythiosis (<60 days of having the disease, some of them with more than 100 days after infection) and three with acute pythiosis (<60 days of having the disease), to conduct a vaccination trial with the vaccine containing the three proteins prepared as in Example 1.

The results indicated that the presence of these three immunodominant proteins remarkably enhanced Mendoza vaccine's curative properties. Of the seven vaccinated horses with chronic pythiosis four were cured, two did not respond, and one initially responded but died later. All of the cured horses developed a mild inflammatory reaction at their vaccination sites. However, the three horses that did not respond to the vaccinations did not develop such a reaction. Those horses had had their infections for more than 100 days and were considered to be anergic. This vaccine also cured all of the early cases of pythiosis.

The results of this experiment suggest that:
1) the presence of the three immunodominant proteins directly enhanced the curative properties of Mendoza's original vaccine which always failed in chronic cases (>60 days) (Mendoza, L., et al., Mycopathologia 119:89–95 (1992)), 2) these proteins are directly involved with the immunotherapeutic properties of Mendoza's vaccine, and 3) these proteins play a role in the immunology of *P. insidiosum* infection.

The findings also confirmed that the response to *P. insidiosum* vaccination is directly related to the immune status of the infected horse. Althoughthe modified vaccine's main attribute is its ability to cure chronic equine pythiosis cases, it retained all of the properties of Mendoza's original vaccine. These include, the production of a mild inflammatory reaction at the site of vaccination in cured but not in unresponsive equines and 100% cure in early cases. The rate of cure using Mendoza's original vaccine was 48%. After addition of the 32K, 30K and 28K proteins, the rate of cure increased to 70%. The enhancement of its curative properties was directly related to the addition of the three prominent proteins to the original vaccine.

EXAMPLE 3

The genes that encode the three major proteins discussed in Example 2 can be cloned to dissect, at a molecular level, the components behind its protective and curative properties. The genes can be used to express the proteins in an expression vector in *E. coli* and combined to provide the improved vaccine.

EXAMPLE 4

This Example shows the use of the *Pythium insidiosum* vaccine (PIV) of Example 1 to successfully treat a Thai boy with a life threatening pythiosis insidiosi arteritis.
Methods A 14 year-old boy presented with a history of progressive headache, mandibular soft tissue swelling, and facial nerve palsy. A computerized tomography scan of the head and neck showed abscesses in the bilateral retromolar fossa and in both ears. A non-sporulating fungus-like organism was isolated in pure culture after surgical drainage of the abscesses. The organism was later identified as *Pythium insidiosum*. Despite treatment with amphotericin B, iodides, ketoconazole, and surgery, the infection progressed. A magnetic resonance imaging (MRI) and magnetic resonance analysis (MRA) of the neck revealed regional lymph node enlargement, stenosis and aneurysm in the external carotid artery. Surgical removal of the aneurysm was performed and *Pythium insidiosum* hyphae were histopathologically observed in the biopsied tissue. A MRA performed later showed stenosis of the internal carotid artery indicating that *Pythium insidiosum* had invaded this artery as well.

Based on the success of the improved vaccine (PIV) in animals with pythiosis insidiosi, vaccination was recommended as a last resort treatment. One hundred microliters of the PIV (2 mg/ml) was subcutaneously injected in the patient's left shoulder and 14 days later the same dose was repeated.
Results Twenty-four hours post vaccination, a wheal and flare reaction had developed at the vaccination site (11 and 8 cm in diameter first and second vaccination, respectively). No other side effects occurred except for itching of the injection site. A second vaccination was performed two weeks later. Four weeks after the first vaccination the patient's headache had disappeared, his facial and left tongue swellings had dramatically diminished, the enlarged cervical lymph node had reduced in size, and the proximal left internal carotid artery stenosis had significantly improved. One year after the first vaccination the boy was considered clinically cured.
Conclusions The dramatic events leading to the cure in this case, indicate that the use of PIV for the immunotherapy of humans with pythiosis insidiosi should be considered in cases that do not respond well to the available chemotherapy.

In particular, a 14 year-old boy was admitted to the Ramathibodi Hospital, Bangkok, Thailand, with a history of 10 days of progressive headache. The illness had begun 16 days before admission in November 1995. Previous to the symptoms, he had developed a small skin injury on the posterior portion of his neck while swimming in a flooded area near a rice field. Four days after the skin injury, he developed three acne-like nodules at the injured site. He then was admitted to a local hospital with a severe headache and soft tissue swelling at the occiput. The swollen mass returned to normal after two days of dexamethazone treatment. The patient, however, continued to have severe headaches and developed a left facial nerve palsy before admission to the Ramathibodi Hospital.

The boy had a history of post splenectomy β-thalassemia hemoglobin E disease of four years duration. He had received at least three blood transfusions per year after his operation. Headache, bilateral facial nerve palsy, and progressively extensive facial cellulitis were recorded on admission. Empirical antibiotic treatment with cefotaxime 100 mg/kg/day and chloramphenicol 75 mg/kg/day were prescribed without success. A computerized tomography (CT) scan of the head and neck showed diffuse cellulitis. Abscesses in the bilateral retromolar fossa and in both ears were also observed. Pain and headache were relieved and the soft tissue swelling subsided after surgical drainage of the abscesses. A non-sporulating fungus-like organism was isolated in pure culture from tissue taken from the left and the right pinna. Because of the possibility of a fungal infection amphotericin B 0.5 mg/kg/day increasing to 1 mg/kg/day was administered. The isolate was later identified as *Pythium insidiosum*.

Although the abscess and cellulitis subsided, one week later, however, the pain and headache reappeared. Swelling of the left side of his tongue was also noticed. Saturated potassium iodide (1 g/ml) 3 ml/day that was increased gradually to 9 ml was prescribed. Despite this treatment, no clinical improvement was observed. Magnetic resonance images (MRI) of the head and neck demonstrated soft tissue involvement and regional lymph node enlargement. Surgical exploration of the left parapharynx and masseteric space was performed. During surgical exploration, the left abnormal cervical lymph nodes and the abnormal left great auricular nerve were removed. Histopathologically, the material showed follicular hyperplasia with sinus histiocytosis and granulomatous inflammation and aseptate hyphal elements of Pythium insidiosum. After failure with amphotericin B and iodides, chemotherapy with 300 mg/day of ketoconazole was initiated. Granulocyte macrophage colony stimulating factor (GM-CSF) was given 5 days immediately post surgical exploration.

The headache and swollen tongue improved after surgical intervention. Although treatment with ketoconazole and iodides continued, pain and headache reappeared three weeks later. A CT angiogram revealed an aneurysm in the left external carotid artery 1.0 cm above the bifurcation and stenosis with irregular walls of the internal carotid artery. A third surgical intervention was performed on Feb. 1, 1996 to remove the aneurysm. The excised tissue was oval in shape 2.5–4 cm in diameter with necrotic-like material within its lumen. Histopathologically, eosinophils, marophages, CD3 positive T-cells, plasma cells, and hyphal elements of Pythium insidiosum were observed within the lumen and the vessel's wall. Pain and headache disappeared immediately after the surgical intervention. Five weeks after surgery, headache and swelling tissue returned. A MRI and a MRA of the neck revealed the persistence of cervical and paracervical lymph node enlargement and persistent stenosis of the left internal carotid artery. These findings suggested that Pythium insidiosum had invaded that artery as well. Surgical removal of the left internal carotid artery was not recommended. Since amphotericin B, ketoconazole, iodides, surgery, and two courses of GM-CSF alone were ineffective in controlling the infection, Pythium insidiosum vaccine (PIV) was suggested as a last resort treatment.

Vaccine Administration

A dose of 100 µl of the 2 mg/ml PIV had been utilized to vaccinate horses with the disease. In successfully treated horses, an inflammatory reaction always developed at the site of vaccination. This inflammatory response indicated not only that the host's immune system was functioning, but it also predicted that the equine probably would be cured by the vaccine. Anergic horses with proven pythiosis insidiosi never developed such a reaction to the vaccine and did not respond to the immunotherapy (Mendoza, L., et al., Mycopathologia 94:123–129 (1986); Newton, J. C., et al., Equine pythiosis: An overview of immunotherapy. Compendium 15:491–493 (1993); and Miller, R. I., et al., J. Am Vet Med Assoc 182:1227–1229 (1983)).

To avoid an excessive immunoresponse in the young boy with Pythium insidiosum arteritis, several dilutions of the original PIV were tested before the trial started. One hundred Al of each PIV dilution (1:100 to 1:100,000) were injected as a skin test on his right forearm. A mild inflammatory reaction was observed only with the 1:100 dilution of the PIV. Thus, the undiluted batch of PIV was selected. One hundred µl of the PIV was subcutaneously injected in the patient's left shoulder.

RESULT

Clinical Course

Twenty hours after vaccination, a wheal and flare reaction had developed at the injection site. Forty-eight hours post vaccination, the wheal reaction attained its maximum size of 11 cm in diameter. No other side effects occurred except for itching at the vaccination site. The skin reaction disappeared 10 days post vaccination. Fourteen days after the first dose, the facial and tongue swelling had diminished. The same day a second vaccination was performed on the patient's right shoulder. Forty-eight hours later the wheal reaction at the vaccination had attained a diameter of eight centimeters.

Two weeks after the second vaccination the patient's headache had disappeared, his facial and left tongue swelling were dramatically diminished, and the enlarged cervical lymph node had reduced in size. For the f first time since his admission the patient's weight had increased by 4.0 kg four weeks post vaccination. The boy was considered clinically cured one year after the first vaccination.

MRI and MRA Findings

A MRI performed 6 weeks after the first vaccination, showed a decrease in the thickening of the soft tissue and less soft tissue enhancement of the left side of his tongue. A MRA of the neck released significant improvement of the stenosis of the proximal left internal carotid artery. The MRI and MRA twelve months post vaccination showed no infiltrations in the soft tissue and a normal left internal carotid artery.

Serology

A serum sample collected during the initial weeks post admission gave a negative results in an ID for pythiosis. Although the ID test in equine pythiosis is a reliable test some negative results have been reported in humans and dogs with proven pythiosis (Chetchotisakd, P., et al., J. Med Assoc Thailand 75:248–254 (1992); and Wanachiwanawin, W., et al., Trans Royal Soc Trop Med Hyg 87:296–298 (1993)). When this serum was tested, before vaccination, in a new Pythium insidiosum-ELISA, positive titers of 1:6,400 were recorded. To monitor the vaccination's progress, sera collected one, two, six and twelve months post vaccination were also evaluated with the ELISA. A decrease in titers from 1:6,400 to 1:800 after 6 months post vaccination indicated that Pythium insidiosum may have been eliminated from the infected tissues, a finding that substantiated the clinical data. The antibody titer against Pythium insidiosum continued to decrease. However, low titers may persist for years as has been previously reported in equines cured by immunotherapy (Mendoza, L., et al., J. Clin Microbiol 30:2980–2983 (1992)).

The response of the patient to PIV vaccine was remarkable. Besides the wheal and flare reaction at the site of vaccination no deleterious side effects developed. Within four weeks after immunotherapy his headaches had disappeared, tissue swelling decreased, and he gained 4.0 Kg in weight. Although the full strength vaccine was used (2 mg/ml) the patient tolerated PIV very well. The success obtained with the immunotherapy in this particular case suggests that PIV may be used as an alternative therapy for human pythiosis insidiosi. This finding is of importance because the available antifungal drugs have little effect on this emerging pathogen. This is the first human pythiosis insidiosi arteritis case treated and cured by the immunotherapeutic PIV.

Traditionally, vaccines have been used only for prophylactic purposes. The use of vaccines for the treatment of diseases, even though an old idea, has only recently received attention (Cohen, J., Science 264:503–505 (1994)). The long-held medical dogma that vaccines are only for prevention has been challenged by scientists working toward the development of immunotherapeutic vaccines against viruses (Burke, D. S., Vaccine 11:883–890 (1993)), parasites (Convit, J., et al., Trans Royal Soc Trop Med Hyg. 87:444–448 (1993)), bacteria (Standford, J. L., Trop Geograp Med 46:93–107 (1994)), fungal (Gudding, R., et al., Can Vet J 36:302–306 (1995)), and parafungal pathogens (Mendoza, L., et al., Mycopathologia 119:89–95 (1992)). Despite impressive data originated by PIV and other curative vaccines, however, strong skepticism exists against the use of therapeutic vaccines as weapons for the treatment of infectious diseases. The skeptics have argued that when a host is invaded by an organism its immune system will mount an immune response that eventually will eliminate the invader. If the immune system fails, the use of drugs is the only avenue to pursue in efforts to save a patient's life. However, the findings generated by PIV and other therapeutic vaccines have indicated that a new line of research is necessary to investigate the mechanism by which these vaccines elicit an immunological reaction that kills the pathogens in infected tissues.

The mechanisms underlying the response to PIV are not well understood. However, based on histopathological and immunological studies in cured equines, it was found that the cellular immune response plays a major role in the clearance of *Pythium insidiosum* from infected tissues (Mendoza, L., et al., Mycopathologia 94:123–129 (1986); Miller, R. I., Aust Vet J 67:377–382 (1981); Newton, J. C., et al., Equine pythiosis: An overview of immunotherapy. Compendium 15:491–493 (1993); and Mendoza, L., et al., Mycopathologia 119:89–95 (1992)). These studies have shown that, after successful immunotherapy, the eosinophilic inflammatory reaction, typical of this disease, gradually changed to a mononuclear immunoresponse. Numerous macrophages, lymphocytes (cytotoxic), and plasma cells had replaced the eosinophilic granuloma. Surprisingly, the mononuclear cells surrounded and killed *P. insidiosum*'s hyphae, eliminating the pathogen from the affected tissues. This observation has been corroborated by the failure to recover *P. insidiosum* from the tissue of equines cured by immunotherapy (Newton, J. C., et al., Equine pythiosis: An overview of immunotherapy. Compendium 15:491–493 (1993) and Mendoza, L., et al., Mycopathologia 119:89–95 (1992)). Based on the PIV data accumulated in the past 15 years in equine pythiosis, it is strongly believed that the *P. insidiosum* vaccine displays to the host's immune system epitopes that are not well presented during natural infection. This scenario is possible since *Pythium insidiosum*'s hyphae are always sequestered inside eosinophilic granulomas. Thus, *Pythium insidiosum* is probably using the degranulated eosinophils to hide important epitopes from the host's immune system.

It is intended that the foregoing description be only illustrative of the present invention and that the present invention be limited only by the hereinafter appended claims.

I claim:

1. An injectable vaccine for treatment of Pythiosis in a mammal including an equine and a human which comprises in a sterile aqueous solution an admixture of:
   (a) intracellular proteins separated from disrupted cells of *Pythium insidiosum* grown in culture medium and from extracellular proteins; and
   (b) extracellular proteins including 28, 30 and 32 kD proteins as determined by SDS-PAGE electrophoresis in a supernatant from the culture medium for growing the cells of the *Pythium insidiosum* which has been separated from the cells wherein the proteins in the admixture of the separated intracellular and extracellular proteins have been mixed with sterile distilled water and dialyzed to remove components less than 10,000 MW, wherein the vaccine is able to cure acute and chronic infections in the mammal including an equine or the human.

2. The vaccine of claim 1 wherein the extracellular proteins have been provided by growing cells of the *Pythium insidiosum* in a culture medium, killing the cells, and then separating the killed cells from the culture medium containing the extracellular proteins and the intracellular proteins have been provided by disrupting the killed cells separated from the extracellular proteins in sterile distilled water and removing the disrupted cells from the intracellular proteins.

3. The vaccine of claim 2 wherein the killed cells have been disrupted by sonication.

4. The vaccine of claim 1 wherein the *Pythium insidiosum* is deposited as ATCC 74446.

5. The vaccine of any one of claims 2 or 3 wherein the culture medium used for growing the cells is Sabouraud dextrose broth.

6. The vaccine of claim 2 wherein the killed cells of *Pythium insidiosum* have been killed with thimersol after the growing in the culture medium.

7. The vaccine of claim 2 wherein the intracellular proteins are separated from the disrupted cells by centrifugation.

8. The vaccine of claim 2 wherein the proteins which are admixed have been separated from the supernatant by being precipitated together using acetone and then the precipitate is dispersed in sterile distilled water.

\* \* \* \* \*